(12) United States Patent
Matusch (10) Patent No.: US 8,535,263 B2
(45) Date of Patent: Sep. 17, 2013

(54) SINGLE-USE INJECTOR CAPABLE OF PUMPING AND HAVING A FLEXURALLY ELASTIC HOUSING

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 270 days.

(21) Appl. No.: 13/134,731

(22) Filed: Jun. 15, 2011

(65) Prior Publication Data

US 2011/0251551 A1  Oct. 13, 2011

Related U.S. Application Data

(63) Continuation-in-part of application No. PCT/EP2009/008614, filed on Dec. 3, 2009.

(30) Foreign Application Priority Data

Dec. 18, 2008  (DE) .......................... 10 2008 063 518

(51) Int. Cl.
  *A61M 5/30* (2006.01)
(52) U.S. Cl.
  USPC .......................................................... 604/68
(58) Field of Classification Search
  USPC .......................................................... 604/68
  See application file for complete search history.

(56) References Cited

U.S. PATENT DOCUMENTS

| | | | |
|---|---|---|---|
| 3,094,989 A * | 6/1963 | Stauffer | 604/138 |
| 3,557,784 A * | 1/1971 | Shields | 604/68 |
| 5,273,544 A * | 12/1993 | van der Wal | 604/134 |
| 5,681,291 A | 10/1997 | Galli | |
| 2001/0039394 A1 * | 11/2001 | Weston | 604/72 |
| 2001/0051789 A1 | 12/2001 | Parsons | |
| 2005/0020984 A1 | 1/2005 | Lesch, Jr. | |
| 2006/0264830 A1 | 11/2006 | Hommann | |
| 2009/0281496 A1 | 11/2009 | Matusch | |
| 2010/0076373 A1 | 3/2010 | Matusch | |

FOREIGN PATENT DOCUMENTS

| | | |
|---|---|---|
| DE | 84 901 A | 6/1895 |
| DE | 84901 A | 6/1895 |
| DE | 831 756 A | 2/1952 |
| EP | 0 518 416 A1 | 12/1992 |
| FR | 1172205 A | 6/1959 |
| FR | 1290671 A | 4/1962 |
| GB | 805 184 A | 12/1958 |
| GB | 805184 | 12/1958 |
| GB | 805184 A | 12/1958 |
| WO | WO 9624398 A1 | 8/1996 |
| WO | WO 00/62846 | 10/2000 |
| WO | WO 2005/070481 | 8/2005 |

* cited by examiner

*Primary Examiner* — Jason Flick
(74) *Attorney, Agent, or Firm* — R. S. Lombard; K. Bach

(57) ABSTRACT

A single-use injector comprising a housing (200) accommodating a mechanical spring energy reservoir (50), a cylinder/piston unit (100), a piston-actuating ram (60) and a trigger unit (80), the spring-locked piston-actuating ram (60) being supported on the housing via support rods, draw hooks or elastic flexural beams. The housing of the injector consists of a thin-walled sheet metal part. Said sheet metal part supports the pretensioned spring energy reservoir and the cylinder/piston unit. The piston (111) of the cylinder/piston unit can be manually displaced by means of a pump rod (140). The single-use injector is compact and has few components, is easy to handle and allows secure storage and functioning. The cylinder/piston unit can be filled when mounted.

11 Claims, 5 Drawing Sheets

Fig. 10  Fig. 11  Fig. 12

SINGLE-USE INJECTOR CAPABLE OF PUMPING AND HAVING A FLEXURALLY ELASTIC HOUSING

CROSS-REFERENCE TO RELATED APPLICATION

This is a continuation-in-part application of pending international application PCT/EP2009/008614 filed Dec. 3, 2009 and claiming the priority of German Application No. 10 2008 063 518.9 filed Dec. 18, 2008.

BACKGROUND OF THE INVENTION

The invention relates to a single-use injector having a housing, in which or on which there are arranged—in each case at least in some areas—at least one mechanical spring energy store, at least one cylinder-piston unit—that can be filled at least temporarily with active substance—, at least one piston-actuating ram and at least one triggering unit, wherein the piston-actuating ram is positioned between the spring energy store and the piston of the piston-cylinder unit, wherein the spring energy store comprises at least one pretensioned spring element, wherein the piston of the cylinder-piston unit can be separately moved by means of a pump rod—when the spring element is pretensioned—, wherein the pump rod can be releasably coupled to the piston or to a piston rod of the piston, wherein the spring-loaded piston-actuating ram is supported by way of housing-side supporting portions and wherein the contact zone situated between the individual supporting portions and the piston-actuating ram represents part of an outwardly forcing wedge gear pairing.

DE 10 2007 031 630 A1 discloses, inter alia, an injector of this type. However, the injector does not have a piston that can be moved by being manually actuated. With the exception of the mechanical spring of the spring energy store, almost all the components of the injector are produced expensively from plastics by injection molding. Components that are subject to high mechanical loads are additionally reinforced with glass fibers.

FR 1 172 205 discloses a spring force-operated multi-use needle injector with an extendable injection needle. In the injector housing of the injector which has no pump rods, the chargeable spring storage structure is held between spring-resilient metal hooks.

US 2001/0051789 A1 discloses a needleless injector whose cylinder-piston unit can be filled via a piston rod integrated into the injector. The spring force-operated injector has a cylindrical plastic housing which consists for example of ABS and which has a release member which is manufactured from a stainless steel strap.

Therefore, the problem addressed by the present invention is that of developing a single-use injector of modular design which, with a small overall size, comprises only a small number of components and, while being easy to handle and inexpensive to produce, ensures safe storage and operation. It is also intended that the cylinder-piston unit of the tensioned single-use injector should be capable of being filled in the fitted state.

SUMMARY OF THE INVENTION

This problem is solved by the features of the main claim. For this purpose, the housing is composed of a thin-walled sheet-metal part which has at least two branches. The two branches each have at the free ends an angled retaining element or a recess—as a means of receiving the cylinder of the cylinder-piston unit. The sheet-metal part that is elastic at least in some areas has at least two pressure rods or at least two tension hooks, the free ends of which are each bent at an angle to form a supporting portion for the piston-actuating ram, or the sheet-metal part has as branches elastic flexural beams, which are each bent away in the shape of a z or an s in the middle area to form a supporting portion for the piston-actuating ram.

The invention provides here, for example, a needleless single-use injector of which the piston-actuating ram is released when the single-use injector is triggered. For this purpose, to pretension and hold the spring energy store, the piston-actuating ram is held with a form fit by way of at least one support rod or tension hook or flexurally elastic branch arranged on the housing or integrated in the housing. Until the single-use injector is used, the support rod(s), tension hook(s) or branch(es) are held in their locked position by a triggering element that surrounds the housing at least in some areas. In order to trigger the injector, the support rod(s), tension hook (s) or branch(es) are released transversely to the triggering direction such that the piston-actuating ram—under the effect of the spring energy store—can move at least approximately parallel to the center line of the single-use injector, in order to discharge the injection solution present in the cylinder of the cylinder-piston unit by way of at least one nozzle.

The housing is in this case a simple, thin-walled sheet-metal part, optionally even just a sheet-metal strip, which supports the mechanical or pneumatic spring of the spring energy store together with a piston-actuating ram and a cylinder-piston unit in cooperation with the triggering element. The punched or cut sheet-metal part, bent several times, can be produced at very little cost from a ferrous material or a non-ferrous metal. Materials that have a high elastic limit, a high tensile strength and a high yield point are ideal. These may optionally also be high-quality plastics and/or composite materials. Almost any material is suitable, even glass or ceramic.

Moreover, the needleless single-use injector has a cylinder-piston unit, which can be filled by a manual pumping movement when the spring store is tensioned. Inter alia, for this purpose a pump rod is coupled from the outside into the piston of the cylinder-piston unit that is arranged in the injector, so that the piston can be moved by means of the pump rod. After proper filling, the cylinder-piston unit can be closed again to the exclusion of germs with a sterile stopper. The pump rod is optionally decoupled and withdrawn from the housing.

BRIEF DESCRIPTION OF THE DRAWINGS

Further details of the invention will become clear from the following illustrative embodiments represented schematically in the drawings, in which.

DETAILED DESCRIPTION OF THE PARTICULAR EMBODIMENTS

Figure 1:
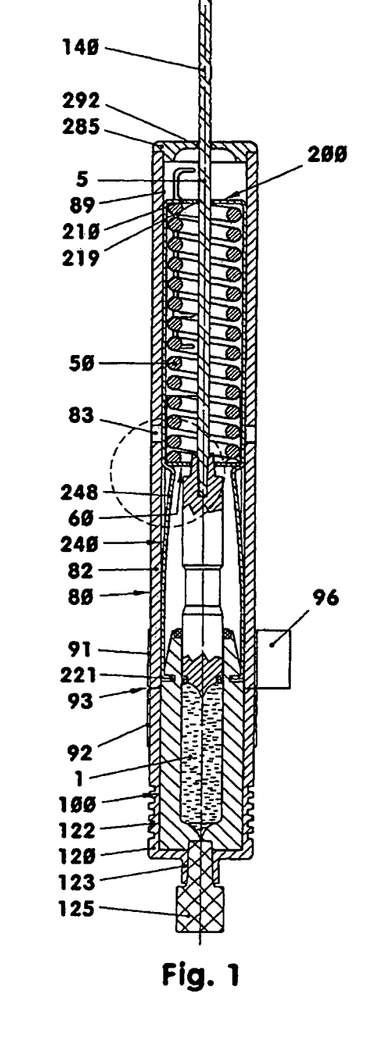
FIG. 1 shows a single-use injector with two support rods.

FIG. 1 shows a single-use or disposable injector with a permanently charged spring energy store. The disposable injector is composed of a housing (200), which is surrounded by a triggering element (82) and by a protective cap (120), a cylinder-piston unit (100), which is pre-filled with an injection solution for example, a piston-actuating ram (60) and a helical compression spring (50) as the spring energy store. The cylinder-piston unit (100), the piston (111) of which can be moved with the aid of a releasable pump rod (140) when the helical compression spring (50) is tensioned, in this case lies for the most part in the protective cap (120).

Figure 4:
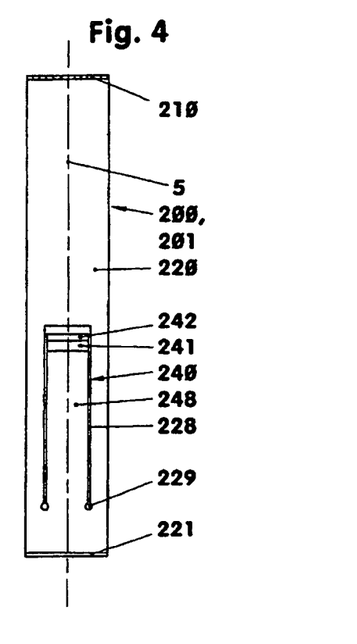
FIG. 4 shows a longitudinal section of the sheet-metal strip, cf. also FIG. 2.

The housing (200) is a sheet-metal strip (201) that has been bent to form a "U", cf. FIG. 4. The angled sheet-metal strip (201), having a width of 18 millimeters, for example, is approximately 240 millimeters long. The sheet-metal strip (201), optionally produced from spring steel, has a wall thickness of 0.5 millimeter, for example. The bent sheet-metal strip (201) is composed of a central end plate (210) and two branches (220) protruding at least approximately perpendicularly from the latter. At their free ends, the branches (220), oriented at least approximately parallel to each other, are each angled inward at an angle of 90 degrees to form a respective retaining element (221) there. The retaining elements (221) are, for example, 1.5 to 3 millimeters long and protrude toward each other. They form a plane that is oriented parallel to the end plate (210).

Instead of the hook-shaped retaining element (221), each branch (220) may be provided with a recess in which the cylinder of the cylinder-piston unit (100) can be suspended in each case by means of a pin.

Figure 5:
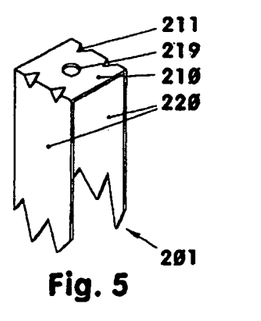
FIG. 5 shows the upper area of the sheet-metal strip.
Figure 6:
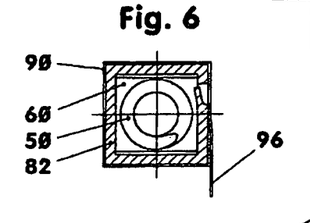
FIG. 6 shows a cross section of FIG. 2.

At the transitions between the end plate (210) and the branches (220), two stiffening beads (211) are in each case pressed in according to FIG. 5. The stiffening beads (211) protrude so far into the end plate (210) that they additionally center the last winding of the helical compression spring (50) on the end plate (210). The end plate (210) has in the middle a bore (292), through which the pump rod (140) is inserted.

A support rod (240), with a width of 9 millimeters for example, is arranged in the lower half of each branch (220), cf. FIG. 4. The support rod (240) is formed by cutting out a u-shaped gap (228), with a width of 0.2 to 0.5 millimeter, for example. In the lower area of each branch (220), that is to say near the retaining elements (221), the gap (228) ends in bores (229) in order to minimize the notch stresses occurring there. In contrast to the substantially planar branches (220), the support rod (240) is bent several times, cf. also FIG. 9. The support rod (240) is composed of a flexural beam (248), a supporting portion (241) and a bearing portion (242). The flexural beam (248) leads the tensioning force of the spring energy store (50) into the branch (220) carrying it. The piston-actuating ram (60) lies on the supporting portion (241) when the single-use injector is in the untriggered state. By way of the bearing portion (242), the support rod (240) rests on the triggering element (82) over a large surface area.

Figure 9:
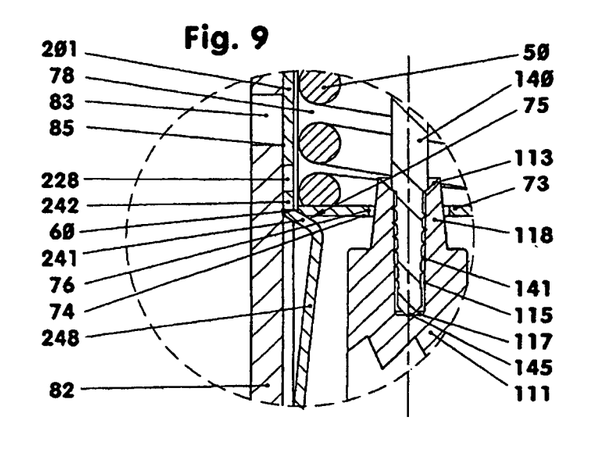
FIG. 9 shows an enlarged detail from FIG. 1.

The supporting portion (241), measuring approximately 1.5 to 3 millimeters in the longitudinal direction, cf. FIG. 9, encloses an angle of 110 to 115 degrees with the flexural beam (248). It is inclined by 60 degrees with respect to the vertical. The bearing portion (242), which is 1 to 2 millimeters wide in the longitudinal direction, encloses an angle of 140° with the supporting portion (241). According to FIGS. 1 and 4, it lies over a large surface area on the triggering element (82). For example, the triggering element (82) has a ceramic lining in the contact area.

The elastic support rods (240) optionally have in the lower area a longitudinal bead—at least approximately parallel to the center line (5)—to increase their resistance to buckling. The support rods (240) always yield resiliently outwards as elastic flexural beams (248) in order not to slow down the lengthening helical compression spring (50) during the triggering action.

The support rods (240) may also be replaced by tension hooks. The latter are likewise delimited from the respective branch (220) by a u-shaped slit. However, the bores (229) in this case lie near the end plate (210). The respective supporting portion of the tension hooks is designed, for example, like the supporting portions (251) of the tension hooks (250) from FIG. 12.

According to FIGS. 1 and 9, the piston-actuating ram (60) lies on the supporting portions (241) of the support rods (240). The piston-actuating ram (60) is in this case a sheet-metal strip that has been bent in the shape of a u and is composed of a middle part, the ram plate (73) and two guide branches (78). The ram plate (73) is oriented parallel to the end plate (210). The guide branches (78) protrude upwards at a right angle. The helical compression spring (50) sits between the guide branches (78). The guide branches (78) are optionally stiffened relative to the ram plate (73) by stiffening beads, cf. the stiffening beads (211) of the sheet-metal part (201) from FIG. 5.

According to FIG. 9, in the area in which it lies on the respective supporting portion (241) of the support rod (240), the ram plate (73) has a 20° bevel (75), for example, in order to ensure contact over a large surface area.

According to FIG. 1, the piston-actuating ram (60) has a width that is slightly smaller—that is to say by ca. 0.1 to 0.3 millimeter—than the normal distance between the two branches (220). Accordingly, the piston-actuating ram (60) is guided laterally on the branches (220). It can be seen in FIG. 2 that the guide branches (78) of the piston-actuating ram (60) are guided with play on the inner wall (89) of the triggering element (82).

According to FIGS. 1 to 3 and 9, inter alia, the ram plate (73) has a central bore (76) for, inter alia, additionally guiding the piston (111) of the cylinder-piston unit (100) rearwardly.

The two support rods (240) subjected to pressure hold the piston-actuating ram (60), by the ram plate (73) thereof, in its pretensioned position, cf. FIGS. 1 and 9. For this purpose, the support rods (240) bear with their supporting portions (241) on the lower 20° bevel (75) of the ram plate (73). The size of the respective contact area between the individual supporting portion (241) and the corresponding 20° bevel (75) lies in the range from 5 to 20 mm$^2$.

The housing (200) made from sheet metal is for the most part surrounded by a triggering element (82) in which it sits and is able to slide. The triggering element (82) is here a square tube which is closed off at the rear end by a cover (285) and is part of a triggering unit (80). The tube (82), which is made of plastic, a polyamide for example, and has a wall thickness of 1.5 to 2.5 millimeters, for example, has two mutually opposite and, for example, rectangular windows (83) or apertures in its central area. The windows (83) have a width of 10.5 millimeters for example, and, in the longitudinal direction, i.e. parallel to the center line (5), have a height of 3.75 millimeters. When the injector is triggered, they in each case receive the bearing portion (242) and the supporting portion (241) of the individual support rod (240), for example completely, cf. FIG. 3.

Figure 7:
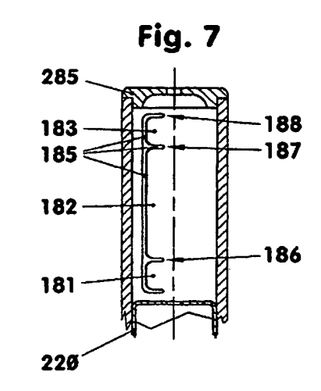
FIG. 7 shows the upper area of the housing during assembly.
Figure 8:
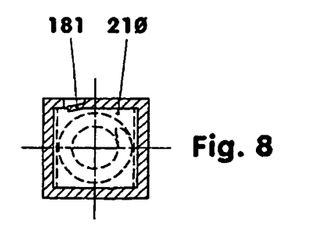
FIG. 8 shows a cross section of FIG. 7.

Three elastic locking tabs (181-183) protruding inward by a few tenths of a millimeter are arranged in the rear area of the square tube (82), cf. FIGS. 7 and 8. The locking tabs (181-183) each have, for example, a rectangular shape. Their wall thickness corresponds to approximately 50% of the wall thickness of the square tube (82). They are delimited on three sides from the wall of the square tube (82) and from the nearest locking tab by gaps (185). The gaps (185) have a width of 0.5 millimeter, for example. The width corresponds to the wall thickness of the end plate (210). At the locations where two gaps (185) meet each other at right angles, the locking tabs (181-183) are rounded.

The eccentrically arranged locking tabs (181-183), formed integrally on the square tube, secure the position of the sheet-metal strip (201) at three locations (186-188). For this purpose, they protrude several tenths of a millimeter into the interior of the triggering element (82). The first location (186) is the gap between the front locking tab (181) and the middle locking tab (182). The end plate (210) is locked in the horizontal gap there, when the sheet-metal strip (201) is assembled, with the helical compression spring (50) clamped between the piston-actuating ram (60) and the end plate (210), for further interim storage.

The second location (187) is the gap between the middle locking tab (182) and the rear locking tab (183). According to FIGS. 1 and 2, the end plate (210) sits here in the case of a disposable injector that has been fully assembled but not yet triggered. The locking of the end plate (210) in this gap prevents withdrawal of the housing (200) from the square tube (82)—after removal of the protective cap (120).

The third location (188) is the gap above the rear locking tab (183). The sheet-metal strip (201) stays in this position after the injector has been triggered, cf. FIG. 3. It is secured there against undesired disassembly of the injector that has then been used.

The respectively upper corners of the locking tabs (181-183)—i.e. the corners facing the cover (285)—optionally have a sharp edge, such that the sheet-metal strip (201) can only be pushed into the square tube (82). A movement in the opposite direction is then impossible, even if great force is exerted.

When the disposable injector has been fully assembled, the windows (83) and the gaps (185) are covered in a dust-proof manner, for example by an optionally elastic film which is permanently affixed by adhesive or shrink-fitted and which may, for example, be inscribed.

In the case of the variants shown here, all the locking elements (181-183) are arranged on the triggering element (82). They fix the position of the end plate (210) relative to the triggering element (82) in some cases temporarily and in some cases permanently. It is also conceivable for the locking elements (181-183) to be replaced by, for example, a cam-like locking element arranged on the housing (200). This element would then engage in corresponding cutouts in the triggering element (82) in order to provide comparable locking positions.

Figure 10:
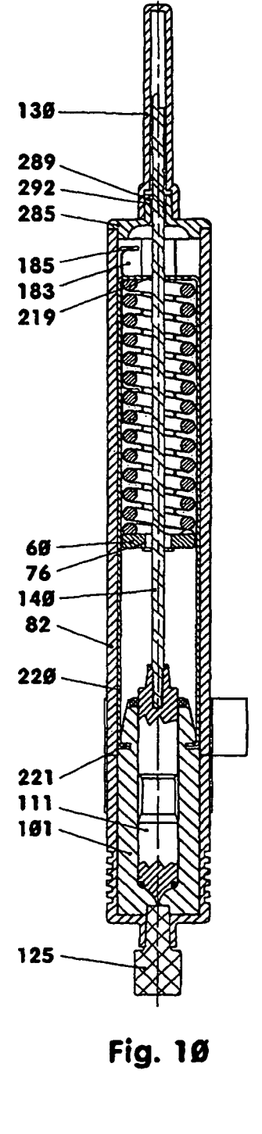
FIG. 10 shows a single-use injector with two tension hooks and a cuboidal ram, the piston in the lower position.

The cover (285) sitting on the rear end of the square tube (82) is, for example, adhesively bonded, welded, locked or compressively joined to the triggering element (82). The cover is optionally also formed integrally on the triggering element (82). The cover (285) has a central bore (292) for the pump rod (140). According to FIG. 10, the cover (285) may also have on its outer side a tubular cap adapter (289). On the latter, a pump rod cap (130) is releasably fitted. The pump rod cap (130) tightly encloses the pump rod (140), which according to FIG. 10 is in its rear position.

In this illustrative embodiment, the cylinder-piston unit (100) is composed of a transparent cylinder (101) which is filled with an injection solution (1) or a solvent, for example water for injection purposes, and in which, according to FIG. 1, a piston (111) sits in its rear position.

The cylinder (101) is, for example, a see-through, thick-walled pot which is produced for example from the amorphous thermoplastic cycloolefin copolymer (COC). The cylinder bore is, for example, cylindrical or frustoconical. In the center of the bore, of which the cylinder base is adapted at least approximately to the contour of the front end face of the piston (111), there is a short cylindrical, nozzle-like bore (106). The diameter thereof is approximately 0.1 to 0.5 millimeter. This bore (106) is one to five times as long as its diameter. It ends in a cylindrical recess (107) in the outer end face (103) at the bottom of the cylinder (101), cf. FIG. 3. It is also optionally possible to arrange two or more nozzle-like bores (106) in the base of the cylinder (101).

Around the recess (107), an adhesive ring (108) firmly adheres to the end face (103). The adhesive ring (108) covers almost the whole of the end face (103) of the cylinder (101).

The spatial outer contour of the cylinder (101) has, for example, a square configuration in the illustrative embodiment. However, it may also be cylindrical. In the central area of the cylinder, the cross section of the outer contour—oriented transversely with respect to the center line (5)—has a square area with a central bore. The cross section is dimensioned such that the cylinder (101) slides with slight play in the interior of the square tube (82).

In the upper quarter directed toward the square tube (82), the cylinder (101) has, in its outer contour, a for example circumferential retaining notch (104) with, for example, a rectangular notch cross section. Above the retaining notch (104), the cylinder (101) narrows in a truncated pyramid shape. The angle enclosed by mutually opposite pyramidal areas is, for example, 20 to 30 degrees. The retaining notch (104) may optionally also be composed simply of two mutually opposite single notches.

The, for example see-through, cylinder (101) has a cylinder inner wall (109) which, in the area of the rear end face of the cylinder, ends in an annular groove (105) for receiving a sealing element (116). The piston (111) and the sealing element (116) close off the filled cylinder interior (110) in a sterile manner.

In this case, the rodless piston (111) sits in the, for example, cylindrical or conical bore of the cylinder (101). The piston (111), produced for example from the Teflon® derivative tetrafluoroethylene/hexafluoroethylene copolymer (FEP), has on its front, at least approximately conically shaped end face an axial annular groove (112) for receiving a sealing ring (114) or a permanently elastic sealing compound. The length of the piston (111) is chosen such that the retracted piston (111), cf. FIG. 3, projects at least 1 millimeter beyond the rear upper edge of the cylinder (101). The central area of the piston (111) is of a narrowed configuration. The circumferentially narrowed area has a length which corresponds to approximately 30% of the overall length of the piston. The narrowed area has a diameter that is 16 to 20% smaller than the maximum inside diameter of the cylinder in the area of the solvent-receiving cylinder interior (110).

The piston (111) has on its rear side, for example, a central, frustoconical pin (118), which protrudes into the bore (76) of the ram plate (73) with play. In the pin (118) there is a central, conical piston recess (115) with the base (117), cf. FIG. 9, for coupling the piston rod (140). The pump rod (140) is optionally also formed integrally on the piston (111). The cone angle of the piston recess (115) is, for example, one degree. For coupling onto the piston (111), the pump rod (140) has at its lower end—according to FIG. 9, inter alia—a conical angular thread (141). The cone angle of the angular thread (141) is, for example, six degrees. The thread turn of the angular thread (141) presses the required counter-thread into the piston recess (115) when the pump rod (140) is screwed in. The screwing-in operation is completed when the narrow tip of the frustoconical end face (145) at the front end of the pump rod (140) comes into contact with the base (117).

The special thread (141), used for coupling purposes, requires only low screwing-in and unscrewing forces. Other releasable couplings can of course also be used, such as for example a key/keyhole system or a simple catch system.

Figure 2:
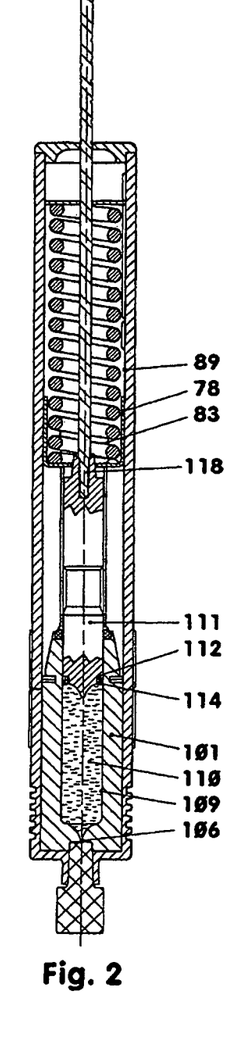
FIG. 2 shows the same as FIG. 1, but pivoted through 90 degrees.
Figure 3:
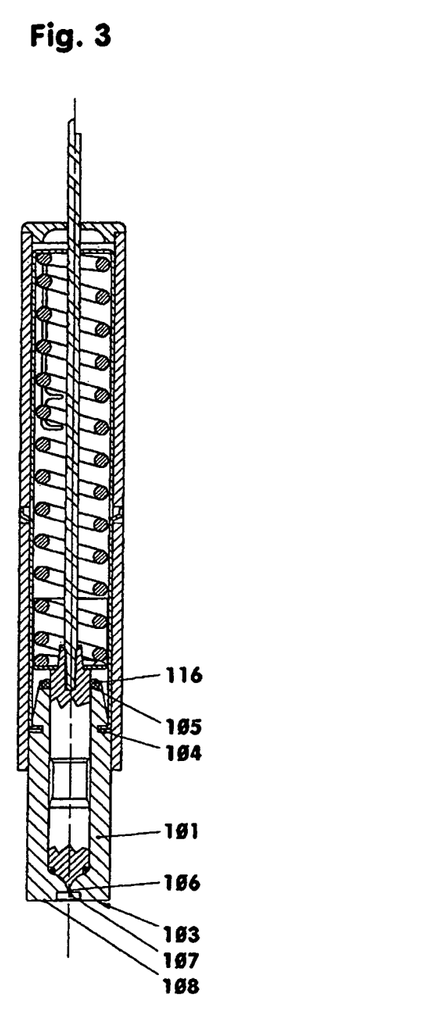
FIG. 3 shows the same as FIG. 1, but after injection.

The pump rod (140), cf. FIGS. 1 to 3, has, for example, a constant cross section over most of its length. Its maximum diameter in the illustrative embodiment is about two millimeters. It is made, for example, of a polyamide reinforced with glass fibers. At its rear end, which protrudes from the bore (292) of the cover (285), it has two differently graduated scales (148) and (149), cf. FIG. 20. The scale (148) is for a cylinder-piston unit (100) of which the cylinder (101) has an average inside diameter of seven millimeters, while the other scale (149) is for a cylinder (101) with an inside diameter of six millimeters. The different-sized cylinders (101) can be inserted into the injector alternately.

Both scales (148, 149) each have horizontal division marks. These division marks lie in planes that are oriented perpendicular to the center line (5). Each division mark has, for example, the length of half the circumference of the pump rod. The division marks of one scale (148, 149) all lie above one another. They may, for example, be colored, black or white division marks or may be formed as notches in the pump rod. Instead of the division marks, dots or numbers may also be used.

The rear end of the pump rod (140) may optionally be provided with a structure, for example transverse or longitudinal grooves, a fluting or the like. The cross section may also be flattened in some areas or have a greater diameter than the area that extends through the piston-actuating ram (60).

Figure 20:
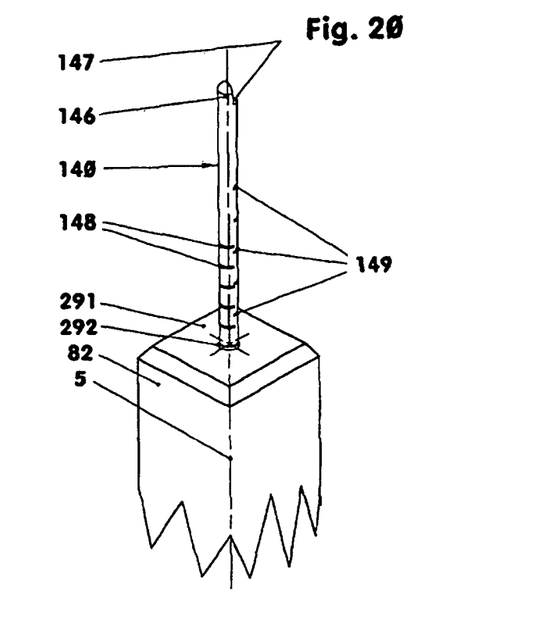
FIG. 20 a diametric view of the rear end of the injector with the pump rod.

According to FIG. 20, the front scale (148), assigned to the larger cylinder, is lengthened by half a cylinder (146) to make the allocation clear. The two lower division marks located directly on the level of the base (86) mark the nominal volume of the respective cylinders (101). The respectively upper division mark indicates that the piston (111) is pushed completely into the cylinder (101). Each of the other division marks of the scales (148, 149) represents 0.1 milliliter, for example.

According to FIGS. 1 and 2, a pot-shaped protective cap (120) is fitted onto the cylinder (101) from underneath. The one-piece protective cap (120), which in geometrical terms is composed in principle of five planar walls, encloses the cylinder (101) laterally with slight play. Its upper, for example planar, end face makes contact with the front end face of the triggering element (82) in the form of a square. The outer wall of the protective cap (120) has a profiling or structure so as to make it easier to pull off from the cylinder (101). In the illustrative embodiment, a groove profile (122) is used as the profiling.

The base of the protective cap (120) has a central adapter opening (123), which ends before the end face recess (107) of the cylinder (101). Together with the recess (107), the adapter opening (123) forms at least approximately a Luer taper. Inserted in the adapter recess (123) is a plastic or rubber stopper (125), which also protrudes in a sealing manner into the recess (107) of the cylinder (101). The protective cap (120) adheres to the cylinder (101) by way of the adhesive ring (108). The latter has a much higher bonding force with respect to the cylinder (101) than with respect to the base of the protective cap (120). To additionally ensure the difference in bonding force, the base is optionally provided with a profile, for example of concentric rings, or a shoulder, such that the contact area with respect to the adhesive ring (108) is smaller than the contact area between the adhesive ring (108) and the cylinder-side end face (103).

The helical compression spring (50) sits pretensioned between the ram plate (73) and the end plate (210) of the sheet-metal strip (201). The spring force is transmitted to the support rods (240) by way of the ram plate (73). Because of the inclination of the bevel (75) of the ram plate (73), the support rods (240) are forced radially outward like a wedge gear, cf. FIG. 9. The bevels (75) make contact with the inclined supporting portions (241) of the support rods (240). The bearing portions (242) lie at least virtually flat on the inner wall of the square tube (82). The square tube (82) thus permanently supports the radial force caused by the wedge gear.

According to FIGS. 1 and 2, the square-shaped triggering element (82) and the protective cap (120) touch at their end faces. As a tamper-evident seal, this area is additionally enclosed by a banderole (90) as a security element. The banderole (90), which can be torn off or separated, is, for example, a paper strip or film strip that is coated on one side with an adhesive. The film strip surrounds once, for example in a single layer, the combination of triggering element (82) and protective cap (120). It temporarily affixes the parts (82) and (120). To prime the injector or remove the protective cap (120)—in preparation for using the injector—the banderole (90) is pulled off or separated in such a way that the adhesive connection between the triggering element (82) and the protective cap (120) is undone. For this purpose, in the illustrative embodiment, the tear-off tab (96) lying in the area of the triggering element (82) is gripped and the banderole (90) is thus unwound, for example in sections. In doing so, the banderole (90) tears at a defined, for example rectilinear, predetermined breaking point (93), which lies exactly in the area of the end faces. Consequently—during priming—only that part (91) of the banderole (90) bearing on the triggering element (82) is removed.

For the assembly of the injector, first the helical compression spring (50) is fitted together with the piston-actuating ram (60) and the sheet-metal strip (201). To do so, the helical compression spring (50) is fitted into the already shaped sheet-metal strip (201) in such a way that one end of the spring comes to bear on the end plate (210). The stirrup-like piston-actuating ram (60) is pushed onto the other end of the spring. Then, with the aid of an assembly device that guides the helical compression spring (50) on the outside or inside, the sheet-metal strip (201) is pushed together between the end plate (210) and the piston-actuating ram (60)—counter to the spring action—to such an extent that the bevels (75) of the end face (74) come to bear behind the supporting portions (241). In doing so, the bearing portions (242) bearing laterally on the piston-actuating ram (60) facilitate the assembly procedure.

The combination of the tensioned spring (50), the sheet-metal strip (201) and the piston-actuating ram (60)—still clamped in the assembly device—is then inserted from underneath into the square tube (82). The insertion procedure is completed when the end plate (210) locks in the gap (186) situated between the locking tabs (181) and (182). In this position (186), the free ends of the branches (220) protrude downward from the square tube (82).

In a further assembly step, the filled cylinder-piston unit (100) is inserted, with the mounted pump rod (140) and the guide pin (118) of the piston (111) to the front, into the square tube (82), closed by the cover (285) and optionally with the pump rod cap (130), in such a way that on the one hand the guide pin (118) engages in the bore (76) of the piston-actuating ram (60) and on the other hand the retaining elements (221) of the branches (220) engage in the retaining notch (104) of the cylinder (101). The pump rod (140) is thereby inserted through the bores (219) and (292). Starting from this position, the square tube (82) is pushed further over the sheet-metal strip (201) until the end plate (210) locks in the gap (187) situated between the locking tabs (182) and (183). In this process, the retaining elements (221) engage securely in the retaining notch (104) and thus fix the cylinder-piston unit (100) unreleasably in the square tube (82). If it is attempted to withdraw the cylinder-piston unit (100) from the triggering tube (82), the retaining elements (221) engaging in the retaining notches (104) are pressed outwardly against the inner wall (89) with a slowing-down and stabilizing effect.

Compared to the assembly step shown in FIG. 1, all that remains to be done is to apply the tamper-evident seal (90) and cover the windows (83) and the gaps (185) by means of an inscribed film.

Figure 12:
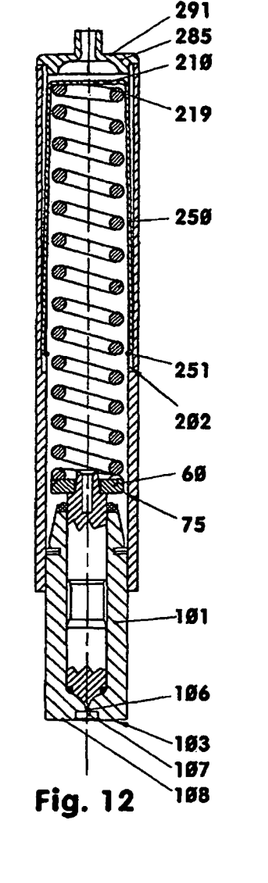
FIG. 12 shows the same as FIG. 11, but without the pump rod and after injection.
Figure 13:
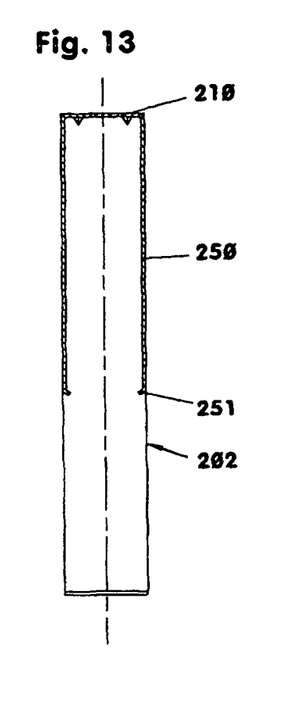
FIG. 13 shows a longitudinal section through the sheet-metal housing.
Figure 14:
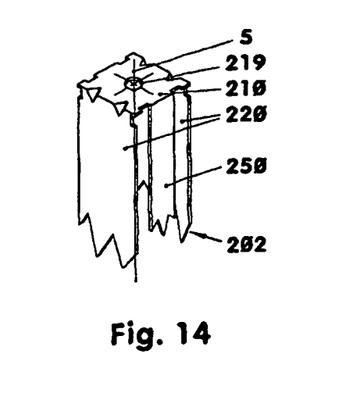
FIG. 14 shows the upper area of the sheet-metal housing.
Figure 15:
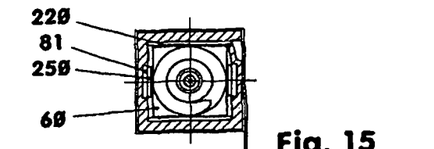
FIG. 15 shows a cross section of FIG. 11.

A second variant of a disposable injector is shown in FIGS. 10 to 15. This injector does not have a sheet-metal strip (201) as its housing, but instead a sheet-metal cross (202), cf. FIGS. 13 and 14. FIG. 14 shows the upper area of the already shaped sheet-metal cross (202). Here, the sheet-metal cross (202) has the already known end plate (210), on which there are arranged two wide, long branches (220) and, offset by 90 degrees—pivoted about the center line (5)—two narrow, short branches (250). The stated size relationships are given only by way of example.

The long, wide branches (220) have the task of holding the cylinder (101) by way of the retaining elements (221), cf. FIG. 10. However, here these branches (220) do not have any support rods.

The short, narrow branches (250), cf. FIG. 13, replace the support rods as tension hooks. At their free, lower ends, the tension hooks (250) shown here each have for this purpose a supporting portion (251), which is obtained by simply bending the end of the tension hook inward, for example by 60 degrees. With the spring energy store (50) tensioned, the here plate-shaped piston-actuating ram (60) lies with its bevels (75) on the supporting portions (251).

Figure 11:
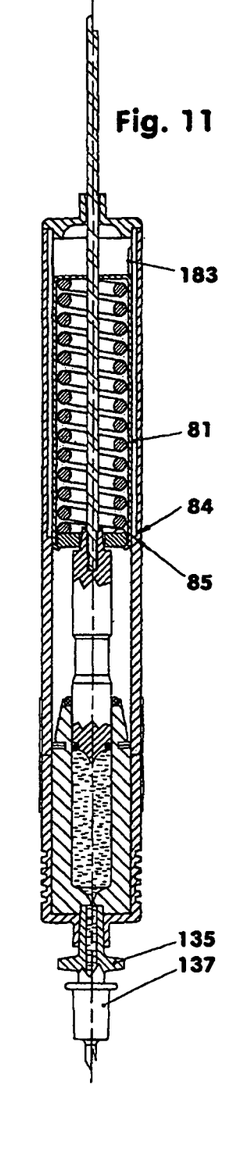
FIG. 11 shows the same as FIG. 10, but pivoted through 90 degrees and with a piston moved into the upper position.

According to FIGS. 10 to 12, the piston-actuating ram (60) is a planar plate with, for example, a square or rectangular end face.

With the spring energy store (50) tensioned, the tension hooks (250) bear on the inner wall of the triggering element (82) below the edges (85) belonging to the longitudinal grooves (81). Here, too, the supporting portions (251) and the bevels (75) form a wedge gear that forces the tension hooks (250) outwards. In the dismantled state, the resiliently elastic tension hooks (250) jut outward. In this way, they yield outward after the injector is triggered—and independently of the action of the wedge gear—so as not to impede the helical compression spring (50) in its change of length.

To allow the tension hooks (250) to be forced outward when the injector is triggered, the, for example square-shaped, triggering element (82) requires the two aforementioned and mutually facing longitudinal grooves (81) on the inner wall (89), cf. FIGS. 11 and 12. Each longitudinal groove (81) ends, in the central area of the triggering element (82), in a return flank (84). As a result of the movement of the triggering element (82) when triggered, the edges (85) arrive below the supporting portions (251) of the tension hooks (250), as a result of which these retreat into the longitudinal grooves (81).

Because of the arrangement of the longitudinal grooves (81) in the square tube (82), the locking tabs (181-183), by way of which the sheet-metal cross (202) is locked in various positions, are shifted in the direction of the inner edge of the next corner.

Instead of the described housing-like sheet-metal cross (202), it is also possible to use a sheet-metal star with six, eight or more branches. For example, a sheet-metal star has an octagonal end plate (210), from which four branches with retaining elements (221) and four other branches with supporting portions (251) are arranged at least approximately perpendicularly. The retaining elements (221) and the supporting portions (251) in this case alternate with one another. The piston-cylinder unit (100) and the triggering element (82) then likewise have here octagonal cross sections, for example. The sheet-metal cross or the sheet-metal star can also be constructed from individual sheet-metal strips, with the sheet-metal strips being welded or riveted, for example, to one another in the area of the end plate (210).

Figure 16:
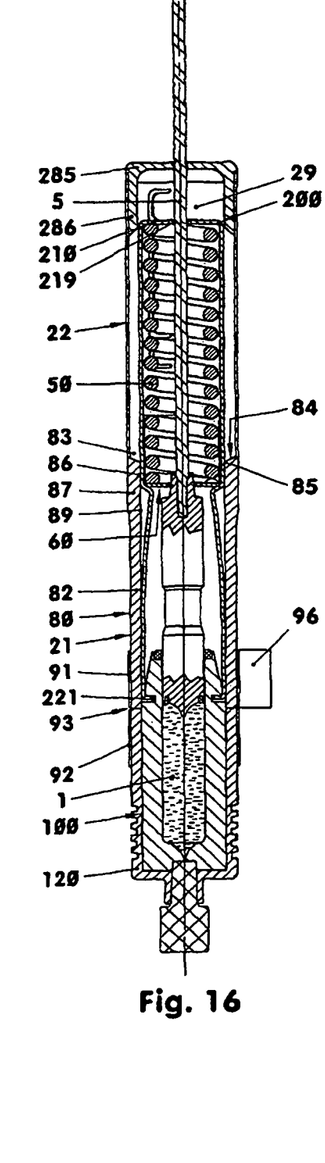
FIG. 16 shows a single-use injector with two bending branches.
Figure 17:
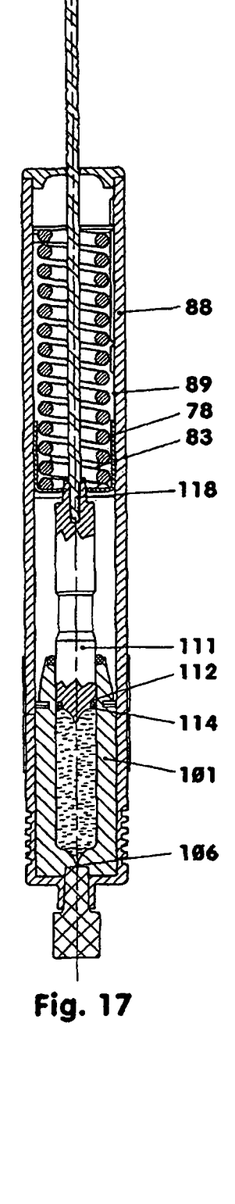
FIG. 17 shows the same as FIG. 16, but pivoted through 90 degrees.
Figure 18:
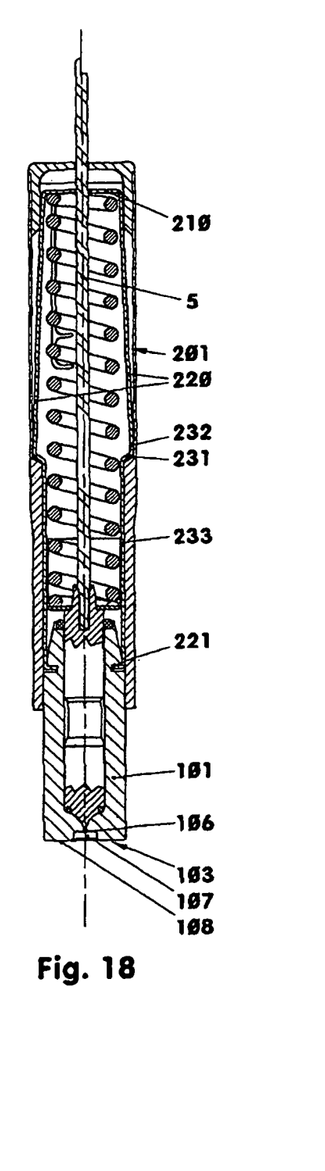
FIG. 18 shows the same as FIG. 1, but after injection.

FIGS. 16 to 18 show a disposable injector capable of pumping and having a housing (200), without tension hooks or pressure supports the housing (200) is in this case a bent sheet-metal strip (201), which is optionally produced from spring steel and is composed of a central end plate (210) and two flexurally elastic branches (220) protruding at least in some areas approximately perpendicularly from the latter. At their free ends, the branches (220), oriented at least approximately parallel to each other, are each angled inward at an angle of 90 degrees to form a respective retaining element (221) there.

In the central area, each branch (220) is bent in the shape of a z or an s, the double-angle-shaped bending being performed mirror-symmetrically with respect to the center line (5), cf. FIGS. 16 and 18. In FIG. 18, the sheet-metal strip (201) is shown in the relaxed state. The central area is in this case a zone that extends above and below the center of the housing (200) by about one quarter of the overall length of the housing.

Each branch (220) is composed of a front retaining portion (233) a central supporting portion (231) and a rear bearing portion (232). The retaining portion (233) is mostly straight and, according to FIG. 16, runs parallel to the center line (5). It is adjoined by the relatively short supporting portion (231). The supporting portion (231), which measures about 1.5 to 3 millimeters in the longitudinal direction of the sheet-metal strip, encloses an angle of 112 to 118 degrees, for example, with the retaining portion (233). It is inclined by 65 degrees with respect to the vertical.

When the disposable injector is not triggered, the piston-actuating ram (60) rests on the supporting portion (231), cf. FIG. 16. It is consequently under tensile load.

The supporting portion (231) is adjoined by the bearing portion (232). It extends as far as the end plate (210). The bearing portion (232) encloses an angle of 113±3 degrees with the supporting portion (231)—according to FIG. 18. It thereby rests on the triggering element (82) over a large surface area.

The two tension-loaded branches (220) hold the piston-actuating ram (60), by the ram plate (73) thereof, in its pre-tensioned position, cf. FIG. 16.

The triggering element (82) surrounding the housing (200) is in this case a tube (82), which is made from plastic, for example a polyamide, is closed to the rear by a cover (285) and has a front area (21) and a rear area (22).

The front area (21), which concerns about the front third of the triggering element (82), has the form of a square tube with the cross section of a square ring. The four side walls (87, 88) each have in this area (21) the same wall thickness of 1.5 to 2.5 mm.

The rear area (22) has the cross section of a rectangular ring, cf. FIG. 16, the side wall (88) being about 5 percent wider than the side wall (87). Arranged in some areas in the side wall (87) is a longitudinal groove (83), which extends as far as the rear end of the triggering tube (82). In the area of the longitudinal groove (83), the wall thickness of the side wall (87) is reduced to 0.5 millimeter, for example. The longitudinal groove (83) ends at the front in a, for example planar, return flank (84), which is inclined by about 75 degrees with respect to the inner wall (89). The inclination has the same orientation as the inclination of the supporting portions (231) of the branches (220) of the sheet-metal strip (201).

In the case of a triggered injector, the longitudinal grooves (83) respectively accept most of the bearing portion (232) and the supporting portion (231) of the individual branch (220), cf. FIG. 18.

Figure 19:
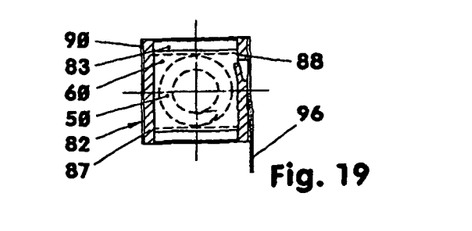
FIG. 19 shows a cross section of FIG. 17.

In the rear area of the triggering tube (82), the locking tabs (181-183)—known from the previous variants—are arranged according to FIG. 17 in the right side wall (88), cf. also FIGS. 16, 18 and 19.

In the case of the variants shown so far, all the locking elements (181-183) are arranged on the triggering element (82). They fix the position of the end plate (210) relative to the triggering element (82) in some cases temporarily and in some cases permanently. It is also conceivable for the locking elements (181-183) to be replaced by at least one locking element arranged on the housing (200). This element then engages, for example, in corresponding cutouts in the triggering element (82) in order to provide comparable locking positions.

At the rear end, the triggering tube (82) is closed by a cover (285), which has two mutually opposite cover tongues (286). They respectively fill the cross section of the longitudinal grooves (83) of the side walls (87) in the rear area of the triggering tube. The cover tongues (286), which are beveled at their free ends toward the interior (29), protrude to such an extent into the triggering tube (82) that they can, according to FIG. 17, support the sheet-metal strip (201) in the area of the end plate (210) laterally with little play, as long as the injector is in the handling state.

The cover is optionally formed integrally on the triggering element (82).

To prepare the described, loadable injectors for use, first the empty cylinder-piston unit (100), cf. FIG. 10, must be filled, with the spring energy store (50) tensioned. For this purpose, on the one hand the pump rod cap (130) is pulled off from the triggering element (82) at the rear and on the other hand the rubber stopper (125) is removed from the adapter opening (123) in the protective cap (120) at the front. Subsequently, for example, an injection needle (137) is connected to the adapter opening (123) by way of a double-cone adapter (135). For filling the cylinder (101), the piston (111) is pulled back with a suction action by means of the pump rod (140). The rear sealing element (116) remains fixed in position on the collar (105), even when the narrowed area of the piston (111) passes the sealing element (116). When the piston (111) has reached its rear position, cf. FIG. 11, the sealing element (116) again bears on the piston (111) in a sterile and radially sealing manner.

After the filling and optionally venting of the cylinder (101), the adapter opening (127) together with the recess (107) can be closed again also at the front in a sterile manner by means of a sterile stopper (125), in order to permit interim storage of the filled injector. The pump rod cap (130) may also be fitted again onto the cap adapter (289).

The variants of the disposable injector described here, with a manually actuated piston (111), may also be combined with a so-called twin-chamber system, as published, inter alia, in DE 10 2008 003 105.

To use the individual disposable injector, it is first primed by detaching the tear-off tab (96) and the rear banderole portion (91), cf. FIG. 1. Subsequently, the protective cap (120) is pulled off from the cylinder-piston unit (100). Then, the injector is positioned on the injection site, with the adhesive ring (108) out in front. The disposable injector is thereby held in the first by the square tube (82). The thumb of the holding hand rests, for example, on the cover (285), for example, as when operating a ballpoint pen.

The square tube (82) is then moved in the direction of the cylinder-piston unit (100). In this process, the triggering element (82) slides linearly down the sheet-metal strip (201), that is to say, in the direction of the injection site. The bearing portions (242) of the support rods (240) slip over the edge (85) and, under the force of the spring element (50), spring outward into the windows (83), in a priming manner, cf. FIGS. 1, 3 and 9. In the case of the variants according to FIGS. 10 to 15, the tension hooks (250) slide over the edges (85), such that the supporting portions (251) engage outwardly in the longitudinal grooves (81). The sheet-metal strip (201), of the variant shown in FIGS. 16 to 19, slips with its bearing portions (232) over the edges (85) so far into the wide longitudinal grooves (83) that the retaining portions (233) come to bear, for example, against the inner wall (89) of the triggering tube (82), cf. FIG. 18.

In the case of all three variants, the supporting portions (231, 241, 251) release the piston-actuating ram (60). The latter shoots downward unimpeded. In doing so, the end face (74) of the ram plate (73) strikes the end face of the piston (111) previously situated a few tenths of a millimeter or a few millimeters away. The piston (111) forces the injection solution or medicament (1) through the nozzle (106), for example, initially at $300 \times 10^5$ Pa, until the cylinder (101) is emptied, cf. FIGS. 3, 12 and 18. The injection procedure is completed when the injection solution (1) is discharged.

The illustrative embodiments show injectors in which the branches (220, 250) of the housing are oriented at least approximately parallel to one another in respective pairs (an angle deviation of ±2 degrees is permissible). The branches (220, 250) lie in parallel planes, wherein the planes—seen in the cross section of the injector—form the mutually opposite sides of a rectangle. The plane of the cross section of the injector lies normal—that is perpendicular—to the center line (5). These sides may also belong to a rhombus, a parallelogram, a trapezoid or an oblique quadrilateral.

Moreover, the branches (220, 250) and the pressure rods (240) are of the same length in respective pairs. This is not absolutely necessary. For example, the pressure rods (240) may be of different lengths if the bearing areas of the piston-actuating ram (60) and the windows or longitudinal grooves (83, 81) are positioned in a correspondingly offset manner.

LIST OF REFERENCE SIGNS

1 injection solution; medicament
5 center line of injector, longitudinal direction
21 front area of (82)
22 rear area of (82)
29 interior
50 spring element, helical compression spring, spring energy store
60 piston-actuating ram
76 bore
73 ram plate
74 end face, lower
75 bevel, 20° bevel
76 bore
78 guide branch
80 triggering unit
81 longitudinal grooves
82 triggering element, square tube
83 windows, apertures, longitudinal grooves
84 return flank
85 edge, sharp-edged
86 contact zone
87 side wall with longitudinal groove (83)
88 side wall without longitudinal groove (83)
89 inner wall
90 tamper-evident seal, banderole, security element
91 rear banderole portion, on (82); part
92 front banderole portion, on (120)
93 predetermined breaking point, perforation
96 tear-off tab
100 cylinder-piston unit
101 cylinder
103 end face
104 retaining notch
105 collar, annular groove
106 bore, nozzle
107 recess in the end face
108 adhesive ring
109 cylinder inner wall
110 cylinder interior
111 piston
112 annular groove
113 end face, rear; cone
114 sealing ring, seal
115 piston recess, bore
116 sealing element in (105)
117 recess base, base of (115)
118 guide pin
120 protective cap
122 groove profile
123 adapter opening
125 stopper
130 pump rod cap
135 double-cone adapter
137 injection needle
140 pump rod
141 conical thread, angular thread
145 end face, frustoconical
146 half cylinder
147 shoulder (for small cylinder)
148 markings, half-notches for large cylinders
149 markings, half-notches for small cylinders
181 locking tab, front; locking element
182 locking tab, middle; locking element
183 locking tab, rear; locking element
185 gap
186 1st location
187 2nd location
188 3rd location
200 housing; sheet-metal part, thin-walled
201 sheet-metal strip; sheet-metal part
202 sheet-metal cross; sheet-metal part
210 end plate
211 beads, stiffening beads
219 end-plate bore
220 branch, long and wide
221 retaining elements
228 gap, u-shaped
229 bores
231 supporting portion
232 bearing portion
233 retaining portion
240 support rods, pressure rods
241 supporting portion
242 bearing portion
248 flexural beam
250 tension hook; branch, short and narrow
251 supporting portion
285 cover
286 cover tongues
289 cap adapter
291 cover upper side (cap base)
292 bore

What is claimed is:

1. In combination with a single-use injector having a housing (200), in which or on which there are arranged—in each case at least in some areas—at least one mechanical spring energy store (50), at least one cylinder-piston unit (100)—that can be filled at least temporarily with active substance—, at least one piston-actuating ram (60) and at least one triggering unit (80), the piston-actuating ram (60) is positioned between the spring energy store (50) and the piston (111) of the piston-cylinder unit (100), the spring energy store comprises at least one pretensioned spring element (50), the piston (111) of the cylinder-piston unit (100) can be separately moved by means of a pump rod (140)—when the spring element (50) is pretensioned, the pump rod (140) can be releasably coupled to the piston (111) or to a piston rod of the piston (111), the spring-loaded piston-actuating ram (60) is supported by way of housing-side supporting portions (231, 241, 251) and the contact zone situated between the individual supporting portions (231, 241, 251) and the piston-actuating ram (60) represents part of an outwardly forcing wedge gear pairing, the improvement which comprises:

the housing (200) is composed of a thin-walled sheet-metal part (201, 202)

the sheet-metal part (201, 202) has at least two branches (220, 250), the at least two branches (220) each have at the free ends an angled retaining element (221) or a recess—as a means of receiving the cylinder (101) of the cylinder-piston unit (100) and the sheet-metal part (201, 202) that is elastic at least in some areas has at least two pressure rods (240) or at least two tension hooks (250), the free ends of which are each bent at an angle to form a supporting portion (241, 251) for the piston-actuating ram (60), or the sheet-metal part (201) has as branches (220) elastic flexural beams, which are each bent away in the shape of a z or an s in the middle area to form a supporting portion (231) for the piston-actuating ram (60).

2. The single-use injector as claimed in claim 1, wherein the housing (200) is composed of a sheet-metal strip (201), the sheet-metal strip (201) is bent in the shape of a u to form two branches (220), the sheet-metal strip (201) has at the two free ends inwardly angled retaining elements (221)—as a bearing for the piston-actuating ram (60), at least one of the branches (220) includes a support rod (240) or a tension hook (250) and the support rod (240) or the tension hook (250) is bent at an angle at its free end, to form a supporting portion (241, 251) for the piston-actuating ram (60).

3. The single-use injector as claimed in claim 1, wherein the branches (220) of the sheet-metal parts (201, 202) are at least five times longer than the width of the branches.

4. The single-use injector as claimed in claim 1, wherein the sheet-metal part (201, 202) is made from a spring steel.

5. The single-use injector as claimed in claim 1, wherein the triggering element (82) is a triggering tube surrounding the sheet-metal part (201, 202).

6. The single-use injector as claimed in claim 5, wherein the triggering element (82) has at least two locations (186, 187) locking notches for temporarily securing the position of the sheet-metal part (201, 202).

7. The single-use injector as claimed in claim 1, wherein the piston-actuating ram (60) is a planar plate (73) with a rectangular base area or is composed of a sheet-metal strip (73, 78) bent in the shape of a u.

8. The single-use injector as claimed in claim 1, wherein, together with each individual support rod (240), tension hook (250) or supporting portion (231) of a branch (220), the piston-actuating ram (60) forms a spline gear in which an axial spring force direction is deflected into a radial supporting force direction.

9. The single-use injector as claimed in claim 1, wherein the individual support rod (240), tension hook (250) or branch (220) is in each case formed integrally on the housing (200) and represents an elastic flexural beam (248).

10. The single-use injector as claimed in claim 1, wherein the pump rod (140) passes in some areas through a bore (76) of the piston-actuating ram (60).

11. The single-use injector as claimed in claim 1, wherein the pump rod (140) protrudes from the rear of the triggering tube (82) or the cover (285) thereof and has one or more scales (148, 149) there.

* * * * *